United States Patent [19]

Redikultsev et al.

[11] 4,324,762

[45] Apr. 13, 1982

[54] APPARATUS FOR STERILIZATION BY STEAM OF FERMENTATION OBJECTS

[76] Inventors: Jury V. Redikultsev, mikroraion "G", dom 19, kv. 133; Leonid A. Litvinenko, mikroraion "AB", dom 8,kv. 74; Svetlana B. Petrikevich, mikroraion "V", dom 30, kv. 54; Taisia S. Chermenskay, mikroraion "G", dom 7, kv. 67; David S. Vershkov, mikroraion "AB", dom 6, kv. 33; Boris F. Nesterov, mikroraion "V", dom 24, kv. 62; Irina V. Bogoroditskaya, mikroraion "AB", dom 6, kv. 41, all of Puschino Moskovskoi oblasti, U.S.S.R.

[21] Appl. No.: 128,366

[22] Filed: Mar. 7, 1980

[30] Foreign Application Priority Data

Jul. 3, 1979 [SU] U.S.S.R. .............................. 2777125

[51] Int. Cl.$^3$ ........................... G05D 9/00; C01B 6/10; C12M 1/12
[52] U.S. Cl. ..................... 422/106; 422/26; 422/295; 422/298; 435/800; 435/311
[58] Field of Search ................. 99/452, 453, 467, 468, 99/483; 126/369.2, 369.3; 426/521, 522; 435/800, 311; 122/4 A, 13 A; 422/106, 22, 26, 295, 298, 299

[56] References Cited

U.S. PATENT DOCUMENTS

| | | | |
|---|---|---|---|
| 3,329,079 | 7/1967 | Palm | 99/453 |
| 3,661,505 | 5/1972 | Frolich | 422/26 |
| 3,687,612 | 8/1972 | Ernst | 422/27 |
| 3,799,220 | 3/1974 | Berry et al. | 99/453 |
| 3,980,131 | 9/1976 | Perle et al. | 422/295 |

OTHER PUBLICATIONS

Buckley, Page, *Techniques of Process Control*, John Wiley and Sons, Inc., New York, 1964, p. 187.

*Primary Examiner*—William F. Smith
*Assistant Examiner*—C. P. Konkol

[57] ABSTRACT

An apparatus for sterilization of fermentation objects by steam comprises a sterilization vessel with a heater, a heat exchanger and an inlet pipe. The apparatus further comprises a buffer vessel communicating with the sterilization vessel via lines including valves. The buffer vessel is provided with its own heater. The apparatus also comprises two gas filters mounted on the heater of the sterilization vessel and interconnected in series through a steam flow rate regulator, one of the filters being connected to the buffer vessel, and the other filter being connected to a pipe adatped to communicate with the fermenter.

5 Claims, 2 Drawing Figures

APPARATUS FOR STERILIZATION BY STEAM OF FERMENTATION OBJECTS

FIELD OF THE INVENTION

The invention relates to apparatus for sterilization by steam of fermentation objects. The disclosed apparatus can be utilized in microbiological, food and medical processes and procedures as well as in research lab practices.

BACKGROUND OF THE INVENTION

Apparatus is known for sterilization by steam of fermentation objects (cf. the U.S. Pat. No. 3,445,341; dated 1969), comprising a sealed chamber—sterilization vessel adapted to contain a solution under investigation, the vessel receiving therein a heater and means for stirring the solution. The sterilization vessel is further provided with a heat exchanger mounted on its surface and adapted to stabilize the selected temperature of the solution under investigation, and also with the inlet and outlet pipes, respectively, for feeding and discharging the solution under investigation.

The operating principle of this prior art apparatus is based on heating the solution contained in the sealed chamber by the heat radiated by the heater which, in its turn, receives its energy from an external steam source. By the development of steam through the heating of the investigated solution a gauge pressure in excess of the atmospheric one is built up within the sealed chamber. A predetermined temperature is maintained within the sealed chamber with aid of a cooling/heating agent circulated through the heat exchanger. The sterilization of the internal space of the sealed chamber takes place simultaneously with the sterilization of the solution contained therein, and when microorganisms are subsequently grown in the chamber, the latter is used as a fermenter.

The prior art apparatus for sterilization by steam of fermentation objects offers only a limited range of applications for research purposes, requiring as it does for its operation an external source of steam. Besides, when a fluid medium is being sterilized, its concentration is varied on account of the condensation of steam in the solution which has a lower temperature.

In the practice of growing microorganisms, it is required more often than not to compose complex nutrient media including various components capable of forming insoluble sediments as the temperature is raised. The general practice in such cases is to sterilize the individual components of the media separately, so as not to vary the concentration of the initial medium. The apparatus of the prior art, however, cannot be used for such separate sterilization of solution, since the sterilization vessel has a unitary volume, so that every new medium added for sterilization would be subjected to the heat treatment jointly with the previously sterilized media, thus forming a complex solution capable of forming a sediment.

Moreover, with the medium including heat-effected components, e.g. glucose, requiring a lower sterilization temperature, the treatment in the prior art apparatus might result in the caramelization of such components, which likewise affects the concentration of the initial medium.

The apparatus of the prior art is inoperable in the process of growing microorganisms continuously, when the continuous supply of a sterile medium into the fermenter is required, because in the course of the fermentation the sterilization vessel operates as the fermenter and would not perform the function of the sterilizer. The apparatus of the prior art is operable for sterilizing fermentation objects, e.g. pumps for feeding a culture suspension, fluid-metering devices, various sensors and connection lines incorporated in the structure of the apparatus itself; however, it cannot be used for sterilizing other fermenters and equipment for supporting fermentation processes. The above factors narrow the range of the applications of the apparatus.

It is an object of the present invention to create an apparatus for sterilization by steam of various fermentation apparatus, e.g. fermenters, communication lines with valves, etc. It is another object of the present invention to provide for sterilization by steam of various liquid nutrient media used both in intermittent and continuous modes of growing microorganisms, while maintaining the initial concentration of such media.

It is still another object of the present invention to provide for sterilization by steam of gas filters.

SUMMARY OF THE INVENTION

The foregoing and other objects are attained in an apparatus for sterilization by steam of fermentation objects, comprising a sterilization vessel equipped with a heater, a heat exchanger, inlet and outlet pipes, a buffer vessel is provided in combination with the sterilization vessel and communicates with the sterilization vessel via lines including valves. The buffer vessel is provided with an additional heater. Gas filters are mounted on the heater of the sterilization vessel and connected in series through a steam flow rate regulator, one filter being connected to the buffer vessel and another filter being connected to the outlet pipe, for communication with a fermenter.

It is expedient to provide the buffer vessel with means for sensing the upper and lower levels of the sterile medium.

It is further expedient that the buffer vessel should include a metering device.

Apparatus for sterilization by steam of fermentation objects, constructed in accordance with the present invention, does not require a central steam supply, having as it does its own heaters, and enables sterilization of various fermentation apparatus, liquid media and gases. The apparatus is operable with a fermenter for conducting intermittent and continuous processes of growing microorganisms; in the continuous process of fermentation, the apparatus provides for separate component by component sterilization of solutions, as well as for periodic sterilization of gas filters; the apparatus enables the sterilization of heat-affectable media.

BRIEF DESCRIPTION OF THE DRAWINGS

The invention will be fully described hereinbelow with reference being made to the to the accompanying drawings, wherein.

DETAILED DESCRIPTION OF THE INVENTION

Figures 1, 2:
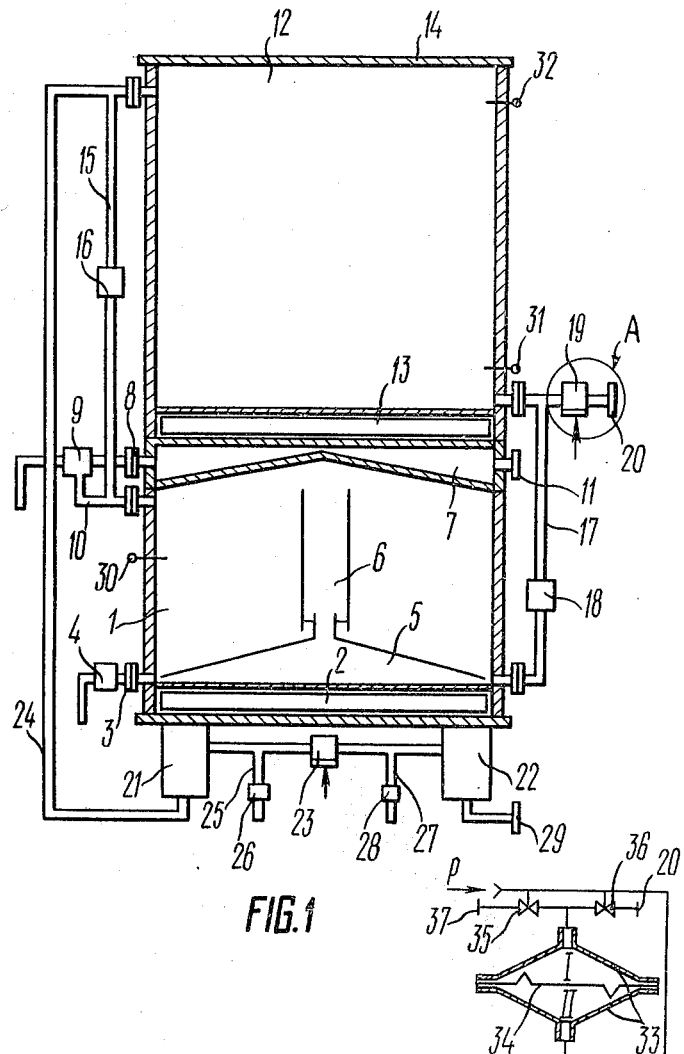
FIG. 1 schematically illustrates a longitudinal sectional view of the apparatus for sterilization by steam of fermentation objects embodying the invention.
FIG. 2 shows on an enlarged scale the area "A" of FIG. 1.

The invention will be further described in connection with one embodiment thereof.

The apparatus generally shown in FIG. 1 of the appended drawings, includes a sterilization vessel 1 adapted to contain therein an initial liquid medium. The lower part of the vessel 1 accommodates a heater 2 and a pipe 3 with a valve 4, through which the sterilization vessel 1 can be charged with the initial liquid medium.

Accommodated within the sterilization vessel 1 is a liquid steam injector made up of a diffuser 5 for steam concentration and an air lift tube 6 for moving the object fluid being sterlized by the action of the steam.

Sealingly mounted in the upper part of the sterilization chamber is a heat exchanger which is in the presently described embodiment is a condenser 7 enabling stabilization at a predetermined temperature of the sterilization or of the investigated medium. The condenser 7 has an inlet pipe 8 with a coolant flow rate regulator 9, communicating via a line 10 with the sterilization vessel 1, and a pipe 11 for draining the coolant from the condenser 7. Mounted atop of the condenser 7 is a buffer vessel 12 accommodating in its lower part an independent heater 13 and having its upper part sealingly closed with a lid 14, the buffer vessel 12 having its upper part communicating via a line 15 including a valve 16 with the upper part of the sterilization vessel 1, enabling the overflow of steam in the fermenter sterilization mode of operation.

The lower part of the buffer vessel 12 communicates with the lower part of the sterilization vessel 1 via a line 17 including a valve 18, enabling the flow of the sterile medium from the sterilization vessel 1 into the buffer vessel 12. The lower part of the buffer vessel 12 further accommodates a metering device 19 with a pipe 20 for connection to a fermenter (not shown), and enabling metering of sterile medium into the fermenter.

The heater 2 of the sterilization vessel 1 has mounted thereon gas filters 21, 22 connected in series through a steam flow rate regulator 23. The filter 21 communicates via a line 24 with the upper part of the buffer vessel 12 and is also associated with a line 25 having a valve 26 by which a gas may be supplied to charge the buffer vessel 12. The filter 22 is associated with a line 27 having a valve 28 for connection to a compressed-air line, and with a pipe 29 directing air through the filter 22 for aeration of the fermenter.

The sterilization vessel 1 is further equipped with a sensor or pickup 30 by which the level of the supplied initial medium is sensed. The buffer vessel 12 is equipped with a sensor 31 by which the lower level of the sterile medium is sensed and with a sensor 32 by which the upper level of the sterile medium is sensed. The level sensors 30, 31, 32 may be in the form of sealed-contact relays with a magnet built into a float following the level of the liquid medium.

The metering device 19 in the presently described embodiment is schematically shown in FIG. 2. The device for metering the liquid medium includes a housing 33 divided into two spaces I and II by a flexible diaphragm 34. The space I is associated with a normally-open pneumatically actuated valve 35 and a normally closed pneumatically actuated valve 36, the pneumatic valve 35 having a pipe 37 for connection to the buffer vessel 12, while the pneumatic valve 36 is associated with the pipe 20 for connection to the fermenter. The space II of the metering device is connected to a compressed air line in parallel with the pneumatic valves 35 and 36, which provides for the operation of the metering device.

To perform the sterilization of fermentation objects, such as a set of utensils, and subsequent sterilization of nutrient media and gas supplied into the fermenter in the process of either intermittent or continuous growing of microorganisms, the gas filter 22 (FIG. 1) is connected via the pipe 29 to the line for feeding the gas into the fermenter for the aeration of the investigated object, i.e. the culture medium. The pipe 20 of the device 19 for metering the sterile medium is connected with the line for feeding the nutrient medium into the fermenter. and the master control (indicated with the arrow line) of the steam flow rate regulator 23 is operated to preset in the space II of the metering device 19 the compressed-air pressure selected to correspond to the steam pressure of the required heat treatment.

The sterilization vessel 1 is filled with distilled water through the open valve 4 to the level of the level sensor 30, whereby the latter responds and sends a signal to close the valve 4 and open the valve 16, and also to energize the heaters 13 and 2.

With the heaters on, the pressure and temperature of steam are built up in the sterilization vessel 1 and in the buffer vessel 12, and upon the pressure attaining the value preset within the master control, the regulator 23 of the steam flow rate would smoothly open, and steam would flow via the buffer vessel 12 where it is additionally heated, the filter 21, the steam flow rate regulator 23 and the filter 22 into the fermenter. The steam pressure in the buffer vessel 12 also acts upon the valve 36 of the metering device 19, and the valve 36 opens the passage for steam via the line for feeding the nutrient medium into the fermenter.

When the time preset for the heat treatment of the apparatus lapses, the heaters 2 and 13 are deenergized, the valve 4 is opened, and the pressure in the sterilization vessel 1 is relieved to the atmospheric value, whereafter the valves 4 and 16 are closed. The system begins to cool down. With the system cooling down, the pressure within the sterilization vessel 1, the buffer vessel 12 and the fermenter drops, the valves 26 and 28 open, and the gas (e.g. air) flows via the filters 21 and 22 into buffer vessel 12 and the fermenter via line 24 and line 29, respectively into the buffer vessel 12, wherefrom it flows into the fermenter via the pipe 29. With the system cooling down, the sterilization vessel 1 remains sealed away.

In the intermittent mode of growing a microorganism culture, the nutrient medium (or else, the solutions of the components making up the nutrient medium) is charged into the sterilization vessel 1 via the open valve 4 to the level of the level sensor 30, whereby the latter responds and sends a signal to close the valve 4 and energize the heater 2.

The master control (not shown in FIG. 1) of the coolant flow rate regulator 9 is set to the compressed-air pressure value corresponding to the steam pressure of the predetermined heat treatment duty.

Within the sterilization vessel 1 being heated, the pressure and temperature of steam therein are raised, and upon the steam pressure attaining the value preset with the master control of the coolant flow rate regulator 9, the coolant is fed into the condenser 7 to provide a temperature gradient across the heater 2 and the surface of the condenser 7. The air-lift injector comes into action and agitates the medium being sterilized. The preselected temperature and pressure in the sterilization vessel 1 are maintained by the corresponding feed rate of the coolant into the condenser 7. When the preset sterilization time elapses, the heater 2 is deenergized, and the valve 18 is opened to pass the sterilized medium under the action of the gauge pressure in the sterilization vessel 1 into the buffer vessel 12. With the passage of the sterilized medium completed, the valve 18 is closed, and the sterilization vessel 1 starts cooling down. Then the next successive amount of the medium is charged for sterilization through the pipe 3 and valve 4, and the cycle is repeated. The sterilized medium is discharged from the buffer vessel 12 into the fermenter through the metering device 19, with the sterilized medium flowing into the space I (FIG. 2) of the metering device via the pipe 37, and filling this space. Then the pressure "P" of compressed air is supplied from the compressed-air line into the space II and to the valves 35 and 36, whereby the valve 35 closes, and the valve 36 opens, so that the metered amount of the sterilized medium is driven by the diaphragm 34 from the space I into the fermenter through the valve 36 and the pipe 20.

In the continuous process of growing a culture of microorganisms, with the sterile medium metered into the fermenter, there are operated several described apparatuses for sterilization by steam of fermentation objects, in a number equalling that of the components making up the medium, the operation of such apparatuses differing from that described hereinabove solely in that the sterile medium is fed periodically from the sterilization vessel 1 (FIG. 1) into the buffer vessel 12 through the valve 18, to fill the vessel 12 to the level of the level sensor 32 which sends a signal to close the valve 18 and to deenergize the heater 2, whereby the apparatus resumes its initial state.

When the level of the sterile medium in the buffer vessel 12 drops to the level of the level sensor 31, the successive amount of the medium is charged into the sterilization vessel 1, and the above described cycle is repeated until the buffer vessel 12 is once again filled with the sterile medium. Thereafter the apparatus resumes its initial state once again. It can be seen from the above that the disclosed apparatus for sterilization by steam of fermentation objects provides for the sterilization of the entire system of growing microorganisms, for maintaining the initial concentration of the sterilized medium, for the sterilization of solutions prepared for microbiological, food and medicine purposes, for the sterilization of media both in intermittent and continuous modes of growing microorganisms, for the sterilization of the gas filters 21 and 22 with live steam, and for their periodic sterilization with dry heat in the process of the heat treatment of liquid media, owing to the filters 21, 22 being mounted on the heater 2.

What we claim is:

1. Apparatus for sterilization by steam of fermentation objects, comprising: a closed sterilization vessel; a first heater mounted on one wall within said sterilization vessel; a condenser mounted on the wall within said sterilization vessel opposite to said one wall; an inlet to said sterilization vessel; a closed buffer vessel; a second heater mounted on a wall within said buffer vessel; lines communicating said buffer vessel with said sterilization vessel; valve means in said lines; at least two gas filters mounted on said first heater; a steam flow rate regulator having an input and an output, the input thereof being connected to one side of the first one of said gas filters and the output thereof being connected to one side of the second one of said gas filters; said first gas filter having its other side communicating with said buffer vessel; a gas outlet pipe connected to the other side of said second gas filter, and a sterile medium outlet pipe connected to said buffer vessel.

2. The apparatus as set forth in claim 1, including sensing means responsive to preset upper and lower levels of the sterile medium within said buffer vessel to permit transfer of fluid between said buffer vessel and said sterilization vessel.

3. The apparatus as set forth in claim 1 or 2, including means for metering the sterile medium, mounted upstream of said sterile medium outlet pipe.

4. The apparatus as set forth in claim 1, wherein said lines communicating with said buffer and sterilization vessel comprise a first conduit extending from the upper portion of said buffer vessel to the upper portion of said sterilization vessel, and a second conduit extending from the lower portion of said buffer vessel to the lower portion of said sterilization vessel.

5. The apparatus as set forth in claim 1, including air-lift means located in said sterilization vessel.

* * * * *